United States Patent [19]

Kalz et al.

[11] Patent Number: 5,639,896

[45] Date of Patent: Jun. 17, 1997

[54] PROCESS FOR THE PREPARATION OF N,N'-DISUBSTITUTED 1,4-DIAMINOANTHRAQUINONES

[75] Inventors: Dietmar Kalz, Neunkirchen; Reinold Schmitz, Odenthal; Karl-Heinz Reinhardt; Josef Schröder, both of Leverkusen; Stephan Michaelis, Odenthal, all of Germany

[73] Assignee: Bayer Aktiengesellschaft, Leverkusen, Germany

[21] Appl. No.: 647,845

[22] Filed: May 3, 1996

[30] Foreign Application Priority Data

May 10, 1995 [DE] Germany ............ 195 17 071.7

[51] Int. Cl.$^6$ ............ C09B 1/20; C09B 1/32; C07C 50/20

[52] U.S. Cl. ............ 552/238; 552/255; 552/258; 552/259

[58] Field of Search ............ 552/238, 255, 552/258, 259

[56] References Cited

U.S. PATENT DOCUMENTS

| | | |
|---|---|---|
| 1,548,768 | 8/1925 | Stowell . |
| 2,152,191 | 3/1939 | Herrett et al. ............ 260/378 |
| 4,083,683 | 4/1978 | Botros ............ 8/39 D |
| 4,306,875 | 12/1981 | De Feo et al. ............ 8/471 |
| 4,614,618 | 9/1986 | Murdock et al. ............ 260/380 |

FOREIGN PATENT DOCUMENTS

| | | |
|---|---|---|
| 0095975 | 12/1983 | European Pat. Off. . |
| 0326866 | 8/1989 | European Pat. Off. . |
| 748995 | 4/1944 | Germany . |
| 1917024 | 10/1969 | Germany . |
| 2209984 | 9/1973 | Germany . |
| 2342469 | 3/1974 | Germany . |
| 1444716 | 8/1976 | United Kingdom . |

OTHER PUBLICATIONS

Chemical Abstract, vol. 80, abstract no. 16445, p. 97, abstract of DE 2,209,984 (1974).

Chemical Abstracts, vol. 72, abstract no. 80352r, pp. 80–81, abstract of DE 1,917,024 (1970).

Patent Abstract of Japan, vol. 011, No. 315, (c–415), abstract of JP 62–101655 (1987).

*Primary Examiner*—José G. Dees
*Assistant Examiner*—Barbara Badio
*Attorney, Agent, or Firm*—Sprung Horn Kramer & Woods

[57] ABSTRACT

A process for the preparation of N,N'-disubstituted 1,4-diaminoanthraquinones has been found which is characterized in that 1,4-dihydroxyanthraquinones are reacted with aliphatic or aromatic amines in the presence of a hydroxycarboxylic acid as a condensation auxiliary.

13 Claims, No Drawings

PROCESS FOR THE PREPARATION OF N,N'-DISUBSTITUTED 1,4-DIAMINOANTHRAQUINONES

The invention relates to an improved process for the preparation of N,N'-disubstituted 1,4-diaminoanthraquinones by reacting 1,4-dihydroxyanthraquinones with amines in the presence of hydroxycarboxylic acids.

N,N'-disubstituted 1,4-diaminoanthraquinones are known, for example, as dyes for plastics and synthetic fibres and as precursors for the preparation of wool dyes. Hitherto, 1,4-diaminoanthraquinones have been prepared by reacting 1,4-dihydroxyanthraquinone (quinizarine) in a mixture with 2,3-dihydro-1,4-dihydroxyanthraquinone (leucoquinizarine) with amines, the reaction having been carried out optionally in the presence of condensation auxiliaries. Examples of known condensation auxiliaries are hydrochloric acid (DE-A-2 342 469) or acetic acid U.S. Pat. No. 4,083,683). However, even when these auxiliaries are used the reaction times and the yields are not optimal.

A process for the preparation of N,N'-disubstituted 1,4-diaminoanthraquinones has now been found which is characterized in that 1,4-dihydroxyanthraquinones are reacted with aliphatic or aromatic amines in the presence of hydroxycarboxylic acids. The hydroxycarboxylic acids to be employed in the process according to the invention are preferably aliphatic or aromatic. In a particular embodiment of the process according to the invention, the aliphatic hydroxycarboxylic acids carry the hydroxyl and the carboxylic acid group on the same carbon atom. The aromatic hydroxycarboxylic acids carry the hydroxyl and the carboxylic acid group preferably at two directly adjacent aromatic carbon atoms.

As aliphatic hydroxycarboxylic acids, particular preference is given to those having 2 to 7 carbon atoms. Examples which can be mentioned are hydroxyacetic acid, lactic acid, malic acid, tartaric acid, citric acid, 2,2-bis-(hydroxymethyl)-propionic acid and galactonic acid. Hydroxyacetic acid is particularly preferred.

As aromatic hydroxycarboxylic acids, ortho-hydroxycarboxylic acids of benzene or naphthalene are of particular importance. Preference is given to salicylic acid and derivatives thereof, for example aliphatic esters, such as $C_1$–$C_4$-alkyl esters, or aromatic esters, such as $C_6$–$C_{10}$-aryl esters, of the formula

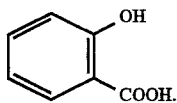

and also naphthalene-ortho-hydroxycarboxylic acids and derivatives thereof, for example aliphatic esters, such as $C_1$–$C_4$-alkyl esters, or aromatic esters, such as $C_6$–$C_{10}$-aryl esters, of the formula

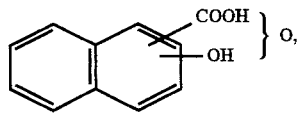

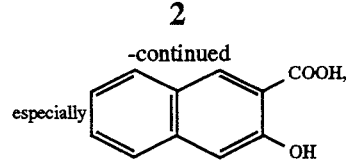

wherein o means ortho, which are optionally substituted by one or more identical or different radicals R in which R represents H, $C_1$–$C_4$-alkyl, especially $CH_3$, halogen, especially Cl, Br and F, OH, CN, COOH or $NO_2$.

Examples which can be mentioned are 2,5-dihydroxy-1,4-benzenedicarboxylic acid and 2-naphthol-3-carboxylic acid.

In this context, the process according to the invention can be carried out in the presence of one or more hydroxycarboxylic acids.

The preferred aliphatic or aromatic amines employed in the process according to the invention are primary. The aliphatic amines can for example be saturated, unsaturated, branched or straight-chain. Particularly preferred aliphatic amines are, for example, those of the following formulae:

$H_2N-CH_2-CH_2-CH_2-CH_3$, $H_2N-CH_2-CH_2-CH-CH_3$,
$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad CH_3$ $H_2N-CH_2-CH-(CH_2)_3-CH_3$, $H_2N-CH_2-CH_2-O-CH_3$,
$\quad\quad\quad\quad\quad\quad C_2H_5$ $H_2N-CH_2-CH_2-CH_2-O-CH_3$, $H_2N-(CH_2)_3-O-C_2H_5$, $H_2N-(CH_2)_3-O-C_4H_9$, $H_2N-(CH_2)_3-O-CH_2-CH-(CH_2)_3-CH_3$ and
$\quad\quad\quad\quad\quad\quad\quad\quad\quad\quad\quad\quad\quad\quad\quad C_2H_5$ $H_2N-(CH_2)_3-O-C_{18}H_{37}$.

With particular advantage, however, the process according to the invention is used to prepare N,N'-disubstituted 1,4-diarylaminoanthraquinones in which the aromatic amines are primary and are, in particular, of the formula

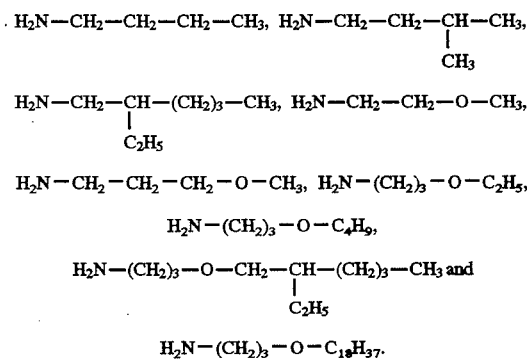

in which
$R_1$, $R_3$ and $R_4$ independently of one another represent H or $C_1$–$C_{12}$-alkyl, especially $C_1$–$C_4$-alkyl, and
$R_2$ represents H or $-SO_2-NH-R_5$, in which $R_5$ represents optionally substituted aryl, especially $C_6$–$C_{10}$-aryl, such as phenyl or naphthyl, or alkyl, especially $C_1$–$C_4$-alkyl, such as methyl, ethyl, propyl or butyl, and where $C_1$–$C_4$-alkyl, OH, halogen, $C_1$–$C_4$-alkoxy and $C_9$–$C_{10}$-aryloxy are preferred as possible substituents.

Particular preference is given to aromatic amines of the formula (I) in which $R_1$ to $R_4$ have the meanings given below.

TABLE

| $R_1$ | $R_2$ | $R_3$ | $R_4$ |
|---|---|---|---|
| H | H | $CH_3$ | H |
| H | H | t.-Bu | H |

TABLE-continued

| R₁ | R₂ | R₃ | R₄ |
|---|---|---|---|
| H | H | H | CH₃ |
| CH₃ | H | H | C₂H₅ |
| CH₃ | H | H | CH₃ |
| C₂H₅ | H | H | C₂H₅ |
| CH₃ | H | CH₃ | CH₃ |
| C₂H₅ | H | CH₃ | C₂H₅ |
| CH₃ | SO₂NH—C₆H₅ | CH₃ | CH₃ |

The 1,4-dihydroxyanthraquinone (quinizarine) employed in the process according to the invention is preferably employed in the mixture with its leuco form, 2,3-dihydro-1,4-dihydroxyanthraquinone (leucoquinizarine), preferably in a ratio of from 10:90 to 90:10, especially 50:50. The mixture of leucoquinizarine and quinizarine can be formed, for example, in situ from the quinizarine by addition of reducing agents such as zinc dust or sodium dithionite. The anthraquinone compounds quinizarine and its leuco form can, however, also be prepared separately. The ratio of amine to anthraquinone compound, i.e. the overall quantity of quinizarine and leucoquinizarine, is preferably chosen such that there are from 1 to 5 mol-equivalents, in particular from 2 to 3.5 mol-equivalents, of amine per anthraquinone (overall quantity of quinizarine and leucoquinizarine) hydroxyl group to be substituted.

In a particularly preferred embodiment, the process according to the invention is carried out in the presence of boric acid. The latter is preferably employed in a quantity of from 0.1 to 1 mol-equivalent, based on the anthraquinone (overall quantity of quinizarine and leucoquinizarine) hydroxyl group to be substituted, in particular from 0.25 to 0.8 mol-equivalents. The process can if desired be carried out in the presence of organic solvents. Examples of suitable solvents are aliphatic alcohols, such as n-butanol and isoamyl alcohol, and also optionally substituted aromatic compounds, such as dichlorobenzene, trichlorobenzene, toluene, xylene, etc. Amine employed in excess can also be used as organic solvent.

The process according to the invention is preferably carried out at a temperature from 60° to 160° C., a rise in temperature towards the end of the reaction preferably being advantageous and involving the removal of the remaining water of reaction from the reaction mixture.

The reaction assisted by a hydroxycarboxylic acid proceeds markedly more quickly than when other condensation auxiliaries are used. The gain in terms of reaction time and yield is particularly great when sterically hindered amines are used, especially aromatic amines of the formula (I) in which $R_1$ and $R_4$ independently of one another denote $C_1$-$C_4$-alkyl. After the end of the condensation reaction according to the invention, the reaction mixture is generally at a temperature which is preferably above the boiling point of water. Temperatures below this are also advantageous, provided the external pressure has been reduced. After the end of the reaction, the reaction mixture is preferably cooled. For oxidation of any leuco compound present, it is preferred to pass air through the reaction mixture. Oxidation can, however, also be carried out with oxidizing agents other than oxygen. This is followed, in general, by isolation of the 1,4-diaminoanthraquinone compound, which is generally precipitated with aliphatic alcohols such as methanol, ethanol, propanol or butanol or with water or alcohol mixtures. The 1,4-diaminoanthraquinone compound is filtered and washed preferably with the alcohols mentioned. This is followed in general by washing with water and, finally, by drying. Precipitation with aqueous hydrochloric acid, as known from U.S. Pat. No. 4,083,683, Example 1, can also be used for isolation.

The yields indicated in the examples are based on the overall quantity of quinizarine and leucoquinizarine employed.

EXAMPLE 1

(Comparison Example Corresponding Essentially to Example 1 from U.S. Pat. No. 4,063,683)

280.0 g (2 mol) of 2-methyl-6-ethylaniline,
40.5 g (0.166 mol) of quinizarine,
40.5 g (0.157 mol) of leucoquinizarine,
12.8 g (0.2 mol) of boric acid and
60.7 g (1.01 mol) of glacial acetic acid
were combined with stirring in a stirring flask with distillation bridge and gas inlet pipe.

The temperature was raised to 145° C. while passing nitrogen in. During this procedure, about 60 g of an acetic acid/water/amine mixture were distilled off. The temperature was held at 145° C. for 12 hours until the starting materials had been consumed. The temperature was lowered to 90° C. and air was passed in for 3 hours after 70 g of KOH had been added. The mixture was subsequently cooled to 70° C. and then 450 ml of methanol were added. After cooling to room temperature, the blue solid was filtered off, washed first with methanol and then with water and, finally, dried in vacuo.

Yield: 107.9 g=70.5% of theory
Reaction time for the condensation reaction: 12 hours.

EXAMPLE 2

280.0 g (2 mol) of 2-methyl-6-ethylaniline,
40.5 g (0.166 mol) of quinizarine,
40.5 g (0.157 mol) of leucoquinizarine,
12.8 g (0.2 mol) of boric acid and
20.0 g (0.15 mol) of hydroxyacetic acid, 57% strength, aqueous
were combined with stirring in a stirring flask with distillation bridge and gas inlet pipe.

The temperature was raised to 145° C. while passing nitrogen in. During this procedure, about 30 g of a mixture of water and a little of the amine employed were distilled off. After 5 hours, quinizarine and leucoquinizarine had reacted completely. The temperature was then lowered to 90° C., 50 g of KOH were added and air was passed in for 3 hours. The mixture was subsequently cooled to 70° C. and 450 ml of methanol were added. After cooling to room temperature, the blue solid was filtered off, washed with methanol and then with water and, finally, dried in vacuo.

Yield: 125.2 g=81.7% of theory
Reaction time for the condensation reaction: 5 hours.

EXAMPLE 3

(Comparison)

300.0 g (2.22 mol) of 2,4,6-trimethylaniline,
40.5 g (0.166 mol) of quinizarine,
40.5 g (0.157 mol) of leucoquinizarine,
12.8 g (0.2 mol) of boric acid and
60.0 g (1.0 mol) of glacial acetic acid
were combined with stirring in a stirring flask with distillation bridge and gas inlet pipe.

The temperature was raised to 145° C. while passing in nitrogen. During this procedure, about 60 g of an acetic acid/water/amine mixture were distilled off. After 8 hours, quinizarine and leucoquinizarine had reacted completely.

The temperature was then lowered to 85° C. At this temperature, 50 g of KOH were added and air was passed in for 4 hours. The mixture was subsequently cooled to 70° C. and 450 ml of methanol were added. After cooling to room temperature, the blue solid was filtered off, washed with methanol and with water and, finally, dried in vacuo.
Yield: 122.5 g=80% of theory
Reaction time for the condensation reaction: 8 hours.

EXAMPLE 4

When the acetic acid in Example 3 was replaced by 20 g of hydroxyacetic acid, 57% strength, a condensation time of only 5 hours and subsequent procedure as in Example 3 gave a yield of 131.7 g=86% of theory.

EXAMPLE 5

When the acetic acid in Example 3 was replaced by 10 g of salicylic acid, a condensation time of 4 hours and subsequent procedure as in Example 3 gave a yield of 132 g=86% of theory.

EXAMPLE 6

When the hydroxyacetic acid in Example 2 was replaced by 14.4 g of lactic acid, 90% strength, a condensation time of 12 hours and subsequent procedure as in Example 2 gave a yield of 127.6 g=81.7% of theory. Using 20 g of malic acid instead of lactic acid, the condensation time to complete conversion was 8 hours and a yield of 117 g=76% of theory was obtained.

EXAMPLE 7

When the hydroxyacetic acid in Example 2 was replaced by 18 g of 3-hydroxy-2-naphthalenecarboxylic acid, a condensation time of 6 hours was required until complete conversion. On proceeding subsequently as in Example 2, the yield was: 121 g=79% of theory.

EXAMPLE 8

When the hydroxyacetic acid in Example 2 was replaced by 23 g of 2,6-dihydroxybenzoic acid, a condensation time of 4 hours and subsequent procedure as in Example 2 gave a yield of 120 g=76.5% of theory. When 2,4-dihydroxybenzoic acid was employed, the yield—at a condensation time of 7 hours—was 110.2 g=72% of theory.

EXAMPLE 9

280 g (1.77 mol) of 2,6-diethyl-4-methylaniline,
40.5 g (0.166 mol) of quinizarine,
40.5 g (0.157 mol) of leucoquinizarine,
12.8 g (0.2 mol) of boric acid and
20.0 g (0.15 mol) of hydroxyacetic acid, 57% strength, aqueous were combined with stirring in a stirring flask with distillation bridge and gas inlet pipe.

The temperature is raised to 145° C. while passing nitrogen over the mixture. During this procedure, about 30 g of a mixture of water and a little of the amine employed were distilled off. After 5 hours, quinizarine and leucoquinizarine had reacted completely. The temperature was then lowered to 90° C., 50 g of KOH in flakes were added and air was passed in for 3 hours. The mixture was subsequently cooled to 70° C. and 450 ml of methanol were added. After cooling to room temperature, the blue solid was filtered off, washed with methanol and then with water and, finally, dried in vacuo.

Yield: 142 g=83% of theory
Reaction time: 5 hours.

We claim:
1. Process for the preparation of N,N'-disubstituted 1,4-diaminoanthraquinones, wherein 1,4-dihydroxyanthraquinones are reacted with aliphatic or aromatic mines in the presence of a hydroxycarboxylic acid.

2. Process according to claim 1, wherein the hydroxycarboxylic acid is aliphatic or aromatic.

3. Process according to claim 1, wherein the hydroxycarboxylic acid if aliphatic carries the hydroxyl and the carboxylic acid group on the same carbon atom and if aromatic carries the hydroxyl and the carboxylic acid group on two directly adjacent aromatic carbon atoms.

4. Process according to claim 1, wherein the hydroxycarboxylic acid is aliphatic and has 2 to 7 carbon atoms.

5. Process according to claim 1, wherein the hydroxycarboxylic acid is an ortho-hydroxycarboxylic acid of benzene or naphthalene.

6. Process according to claim 5, wherein the ortho-hydroxycarboxylic acid is of the formula

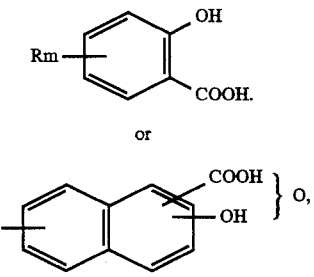

wherein o means ortho, wherein R independently of one another represent H, $C_1$–$C_4$-alkyl, halogen, Cl, Br and F, OH, CN or $NO_2$ and m=0–4 and n=0–6.

7. Process according to claim 6, wherein R represents Cl, Br and F, OH or CN.

8. Process according to claim 6, wherein the ortho-hydroxycarboxylic acid is of the formula

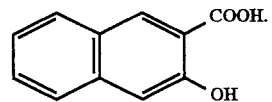

9. Process according to claim 1, wherein the hydroxycarboxylic acid employed is hydroxyacetic acid, lactic acid, malic acid, tartaric acid, citric acid, 2,2-bis-(hydroxymethyl)-propionic acid, galactonic acid, salicylic acid, 2,5-dihydroxy-1,4-benzenedicarboxylic acid, and/or 2-naphthol-3-carboxylic acid.

10. Process according to claim 1, wherein the aliphatic or aromatic amines are primary.

11. Process according to claim 1, wherein the aromatic amines are of the formula

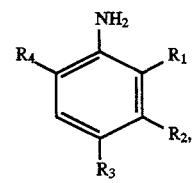

(I)

in which $R_1$, $R_3$ and $R_4$ independently of one another represent H or $C_1$–$C_{12}$-alkyl and $R_2$ represents hydrogen or —$SO_2$—NH—$R_5$, in which $R_5$ represents optionally substituted aryl or alkyl.

12. Process according to claim 1, wherein $R_1$, $R_3$ and $R_4$ independently of one another represent H or $C_1$–$C_4$-alkyl.

13. Process according to claim 1, wherein the reaction carried out in the presence of boric acid.

* * * * *

UNITED STATES PATENT AND TRADEMARK OFFICE
CERTIFICATE OF CORRECTION

PATENT NO. : 5,639,896
DATED : June 17, 1997
INVENTOR(S) : Kalz, et al.

It is certified that error appears in the above-indentified patent and that said Letters Patent is hereby corrected as shown below:

Col. 6, line 7   Delete " mines " and substitute -- amines --

Col. 7, line 3   Delete claim " 1 " and substitute -- 11 --

Col. 8, line 1   After " reaction " insert -- is --

Signed and Sealed this

Seventeenth Day of February, 1998

Attest:

BRUCE LEHMAN

Attesting Officer    Commissioner of Patents and Trademarks